(12) United States Patent
Dong

(10) Patent No.: US 11,246,540 B2
(45) Date of Patent: Feb. 15, 2022

(54) PULSE SIMULATOR, PULSE SENSOR, HAPTIC MEDICAL DEVICE HAVING PULSE SIMULATOR, AND METHOD FOR HAPTIC PULSE DETECTION

(71) Applicant: BOE TECHNOLOGY GROUP CO., LTD., Beijing (CN)

(72) Inventor: Wenchu Dong, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 943 days.

(21) Appl. No.: 15/774,931

(22) PCT Filed: Dec. 7, 2017

(86) PCT No.: PCT/CN2017/115080
§ 371 (c)(1),
(2) Date: May 9, 2018

(87) PCT Pub. No.: WO2018/205585
PCT Pub. Date: Nov. 15, 2018

(65) Prior Publication Data
US 2021/0161481 A1   Jun. 3, 2021

(30) Foreign Application Priority Data

May 8, 2017   (CN) .......................... 201710316666.1
Jun. 30, 2017   (CN) .......................... 201710526262.5

(51) Int. Cl.
*A61B 5/00* (2006.01)
*G16H 50/50* (2018.01)
(Continued)

(52) U.S. Cl.
CPC ............ *A61B 5/7278* (2013.01); *A61B 5/022* (2013.01); *A61B 5/026* (2013.01);
(Continued)

(58) Field of Classification Search
CPC ........ A61B 5/02; A61B 5/022; A61B 5/02133
See application file for complete search history.

(56) References Cited

U.S. PATENT DOCUMENTS

| 2003/0212335 A1 | 11/2003 | Huang |
| 2011/0037836 A1 | 2/2011 | Chang |

FOREIGN PATENT DOCUMENTS

| CN | 1638693 A | 7/2005 |
| CN | 101138488 A | 3/2008 |

(Continued)

OTHER PUBLICATIONS

International Search Report & Written Opinion dated Mar. 5, 2018, regarding PCT/CN2017/115080.
(Continued)

*Primary Examiner* — Puya Agahi
(74) *Attorney, Agent, or Firm* — Intellectual Valley Law, P.C.

(57) ABSTRACT

The present application discloses a pulse simulator. The pulse simulator includes a pulse simulation assembly configured to receive a pulse simulation signal and simulate a pulse of a living body based on the pulse simulation signal. The pulse simulation assembly includes a mounting plate; a plurality of retractable bolts on the mounting plate; and a plurality of drivers coupled to the plurality of retractable bolts. Each of the plurality of retractable bolts has a first end attached to the mounting plate and a second end opposite to the first end. Each of the plurality of drivers is configured to drive one of the plurality of retractable bolts to retract and extend between a first position and a second position thereby adjusting a distance between a simulated skin portion and the mounting plate in a region corresponding to the one of the plurality of retractable bolts.

9 Claims, 4 Drawing Sheets

(51) Int. Cl.
*A61B 5/02* (2006.01)
*A61B 5/021* (2006.01)
*A61B 5/022* (2006.01)
*A61B 5/026* (2006.01)

(52) U.S. Cl.
CPC ...... *A61B 5/02007* (2013.01); *A61B 5/02035* (2013.01); *A61B 5/02141* (2013.01); *A61B 5/7455* (2013.01); *G16H 50/50* (2018.01); *A61B 5/02* (2013.01); *A61B 5/02133* (2013.01)

(56) References Cited

FOREIGN PATENT DOCUMENTS

| | | |
|---|---|---|
| CN | 101773382 A | 7/2010 |
| CN | 101987014 A | 3/2011 |
| CN | 101995692 A | 3/2011 |
| CN | 102266220 A | 12/2011 |
| CN | 102988031 A | 3/2013 |
| CN | 103417200 A | 12/2013 |
| CN | 103431842 A | 12/2013 |
| CN | 104825142 A | 8/2015 |
| CN | 105342582 A | 2/2016 |
| CN | 105892971 A | 8/2016 |
| CN | 205594505 U | 9/2016 |
| EP | 1074216 A1 | 2/2001 |

OTHER PUBLICATIONS

Second Office Action in the Chinese Patent Application No. 201710526262.5, dated Sep. 27, 2019; English translation attached.
First Office Action in the Chinese Patent Application No. 201710316666.1, dated Jan. 25, 2019; English translation attached.

PULSE SIMULATOR, PULSE SENSOR, HAPTIC MEDICAL DEVICE HAVING PULSE SIMULATOR, AND METHOD FOR HAPTIC PULSE DETECTION

CROSS-REFERENCE TO RELATED APPLICATION

This application is a national stage application under 35 U.S.C. § 371 of International Application No. PCT/CN2017/115080, filed Dec. 7, 2017, which claims priority to Chinese Patent Application No. 201710526262.5, filed Jun. 30, 2017, and Chinese Patent Application No. 201710316666.1, filed May 8, 2017. Each of the forgoing applications is herein incorporated by reference in its entirety for all purposes.

TECHNICAL FIELD

The present invention relates to medical device, more particularly, to a pulse simulator, a pulse sensor, a haptic medical device having a pulse simulator, and a method for haptic pulse detection.

BACKGROUND

Remote diagnosis of patients has been become a topic for research and development in recent years. Remote diagnosis is an act of diagnosing a given symptom, issue, or problem from a distance. In remote diagnosis, the patient need not be co-located with the medical professional, but can be separated by physical distance.

SUMMARY

In one aspect, the present invention provides a pulse simulator, comprising a pulse simulation assembly configured to receive a pulse simulation signal and simulate a pulse of a living body based on the pulse simulation signal; wherein the pulse simulation assembly comprises a mounting plate; a plurality of retractable bolts on the mounting plate; and a plurality of drivers coupled to the plurality of retractable bolts; wherein each of the plurality of retractable bolts has a first end attached to the mounting plate and a second end opposite to the first end; and each of the plurality of drivers is configured to drive one of the plurality of retractable bolts to retract and extend between a first position and a second position thereby adjusting a distance between the simulated skin portion and the mounting plate in a region corresponding to the one of the plurality of retractable bolts.

Optionally, the pulse simulator further comprises a simulated skin portion coupled to the pulse simulation assembly; wherein the second end of each of the plurality of retractable bolts is configured to be in contact with the simulated skin portion; and the pulse simulation assembly is configured to simulate the pulse of a living body on the simulated skin portion based on the pulse simulation signal.

Optionally, the plurality of retractable bolts are an array of a plurality of retractable bolts comprising a plurality of rows and a plurality of columns.

Optionally, each of the plurality of retractable bolts comprises an actuating stem; a sleeve surrounding the actuating stem; and a coil around an outer surface of the sleeve; wherein the actuating stem comprises a magnetic main body; the magnetic main body has an external thread on its outer surface; the sleeve has an internal thread on its inner surface; a first end of the magnetic main body threadedly engaged with the sleeve; one of the plurality of driven is configured to provide a current to the coil to generate a magnetic field in the coil.

Optionally, the actuating stem further comprises a contact cap on a second end of the magnetic main body opposite to the first end of the magnetic main body; and the contact cap has a convex curved surface protruding outward along a direction away from the mounting plate.

Optionally, the plurality of drivers are on the mounting plate.

Optionally, the pulse simulator further comprises a plurality of pressure sensors configured to detect a pressure applied on the simulated skin portion and generate a pressure simulation signal based on the pressure applied on the simulated skin portion.

Optionally, the pulse simulation signal comprises a pulse wave signal.

Optionally, the pulse simulation signal further comprises one or any combination of a plurality of signals respectively indicating a blood vessel shape, blood viscosity, and blood flow speed.

In another aspect, the present invention provides a pulse sensor, comprising an inflatable cuff; a plurality of pulse wave pressure sensors on an inner surface of the inflatable cuff and configured to detect a pulse wave and generate a pulse wave signal; and a first controller configured to generate a pulse simulation signal based on the pulse wave signal from the plurality of pulse wave pressure sensors.

Optionally, tins pulse simulation signal comprises a signal indicating a blood vessel shape; the pulse wave signal comprises a signal indicating a frequency of a pulse wave, a signal indicating an amplitude of the pulse wave, and an address of one of the plurality of pulse wave pressure sensors detecting the pulse wave; the first controller is configured to determine the blood vessel shape based on the address of the one of the plurality of pulse wave pressure sensors.

Optionally, the pulse sensor further comprises a plurality of reference pressure sensors on the inner surface of the inflatable cuff and configured to detect a pressure applied by the inflatable cuff; wherein the plurality of reference pressure sensors are configured to generate a stop signal based on a determination that the pressure applied by the inflatable cuff detected by the plurality of reference pressure sensors is greater than a threshold value.

Optionally, the pulse sensor further comprises a pump for inflating five inflatable cuff; wherein a control terminal of the pump is coupled to an output terminal of the first controller; an output terminal of each of the plurality of reference pressure sensors is coupled to an input terminal of the first controller; and the first controller is configured to control the pump to discontinue inflating the inflatable cuff upon receiving the stop signal from the plurality of reference pressure sensors.

Optionally, the pulse simulation signal comprises at least one of a signal indicating blood viscosity and a signal indicating blood flow speed; the pulse sensor further comprises an optical detection sensor on the inner surface of the inflatable cuff and configured to detect at least one of the signal indicating blood viscosity and the signal indicating blood flow speed.

In another aspect, the present invention provides a haptic medical device, comprising the pulse simulator described herein or fabricated by a method described herein; and a second controller coupled to the plurality of drivers; wherein the second controller is configured to receive the pulse simulation signal and transmit the pulse simulation signal to the plurality of drivers.

Optionally, the haptic medical device thriller comprises a display device for visual data communication.

Optionally, the haptic medical device Anther comprises the pulse sensor described herein or fabricated by a method described herein; wherein the second controller is communicatively coupled to the first controller and is configured to receive the pulse simulation signal from the first controller.

Optionally the pulse simulator further comprises a plurality of pressure sensors configured to detect a pressure applied on the pulse simulation assembly and generate a pressure simulation signal based on the pressure applied on the pulse simulation assembly; the pulse simulator is configured to detect a pressure applied on the simulated skin portion and generate a pressure simulation signal based on the pressure applied on the simulated skin portion; the second controller is configured to receive the pressure simulation signal and transmit the pressure simulation signal to the first controller; and the first controller is configured to generate a threshold value for a threshold pressure based on the pressure simulation signal received from the second controller.

In another aspect, the present invention provides a method for haptic pulse detection, comprising connecting a pulse simulator and a pulse sensor at different locations to a computer network; detecting a pulse wave and generate a pulse wave signal using the pulse sensor; generating a pulse simulation signal based on the pulse wave signal; transmitting the pulse simulation signal to the pulse simulator; and simulating a pulse based on the pulse simulation signal on a simulated skin portion using the pulse simulator.

Optionally, the method of further comprises detecting a pressure applied on the simulated skin portion; and generating a pressure simulation signal based on the pressure applied on the simulated skin portion.

BRIEF DESCRIPTION OF THE FIGURES

The following drawings are merely examples for illustrative purposes according to various disclosed embodiments and are not intended to limit the scope of the present invention.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

A conventional pulse simulator uses elastic materials such as rubber to make synthetic blood vessels, into which a liquid is filled by a pump. The pumping action of the pump simulates a pulse in the convention pulse simulator. However, blood vessels in different individuals have different sizes (e.g., diameters). Blood viscosities in different individuals typically vary a lot. The conventional pulse simulator is not capable of simulating different pulse states due to these different physiological states of different individuals. Thus, accurate, personalized pulse simulation has not been made possible in the conventional pulse simulator.

Accordingly, the present disclosure provides, inter alia, a pulse simulator, a pulse sensor, a haptic medical device having a pulse simulator, and a method for haptic pulse detection that substantially obviate one or more of the problems due to limitations and disadvantages of the related art. In one aspect, the present disclosure provides a pulse simulator. In some embodiments, the pulse simulator includes a pulse simulation assembly configured to receive a pulse simulation signal and simulate a pulse of a living body based on the pulse simulation signal. Optionally, the pulse simulation assembly includes a mounting plate; a plurality of retractable bolts on the mounting plate; and a plurality of drivers coupled to the plurality of retractable bolts. Optionally, each of the plurality of retractable bolts has a first end attached to the mounting plate and a second end opposite to the first end. Optionally, each of the plurality of drivers is configured to drive one of the plurality of retractable bolts to retract and extend between a first position and a second position thereby adjusting a distance between the simulated skin portion and the mounting plate in a region corresponding to the one of the plurality of retractable bolts. Optionally, the pulse simulator further includes a simulated skin portion coupled to the pulse simulation assembly. Optionally, the simulated skin portion is wrapped on the plurality of retractable bolts, Optionally, the second end of each of the plurality of retractable bolts is configured to be in contact with the simulated skin portion. The pulse simulation assembly is configured to simulate the pulse of a living body on the simulated skin portion based on the pulse simulation signal. Optionally, the pulse simulator is a haptic pulse simulator configured to simulate a pulse being detected in an individual at a remote location, e.g., in real time.

Figure 1:
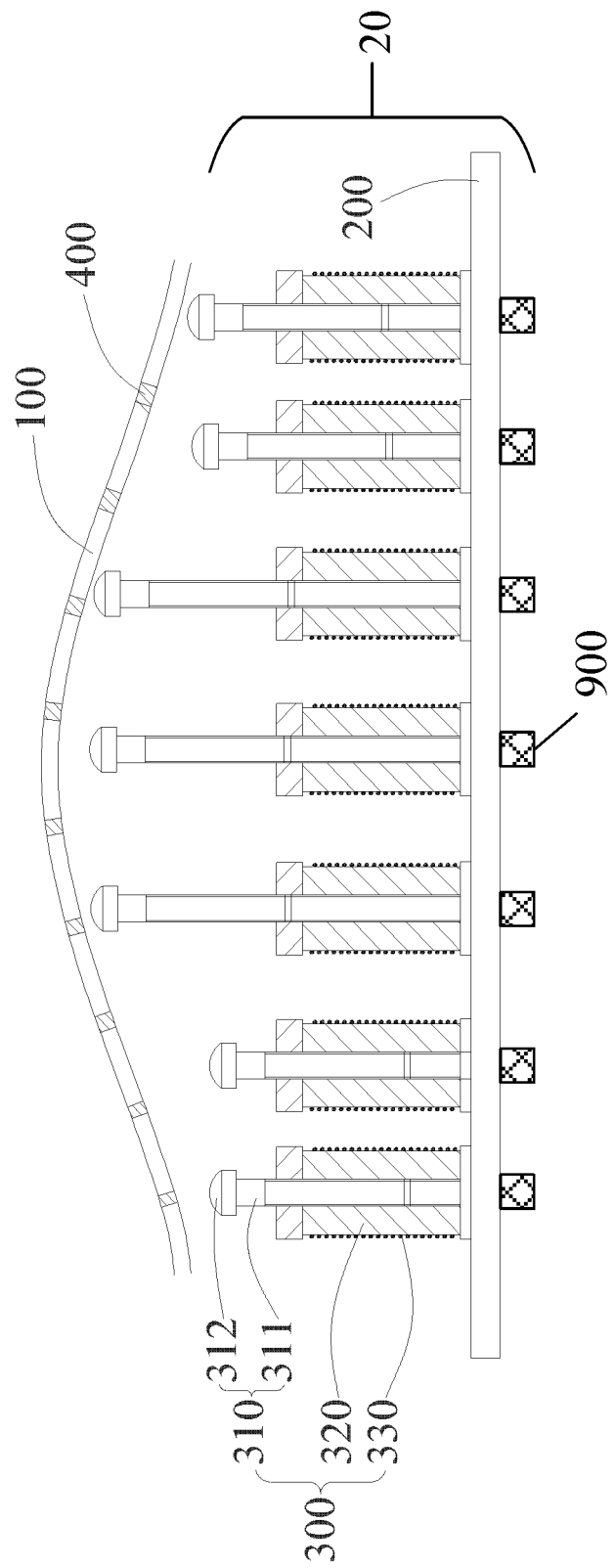
FIG. 1 is a schematic diagram illustrating the structure of a pulse simulator in some embodiments according to the present disclosure.

FIG. 1 is a schematic diagram illustrating the structure of a pulse simulator in some embodiments according to the present disclosure. Referring to FIG. 1, the pulse simulator in some embodiments includes a simulated skin portion 100 and a pulse simulation assembly 20 coupled to the simulated skin portion 100. The pulse simulation assembly 20 is configured to receive a pulse simulation signal and simulate a pulse on the simulated skin portion 100 based on the pulse simulation signal. For example, the simulated pulse causes the simulated skin portion 100 to protrude out and then fall back in in one or more regions of the simulated skin portion 100. The actions of protruding out and falling back in in the one or more regions of the simulated skin portion 100 simulates the pulse of an individual (e.g., a patient). The present pulse simulator is capable of simulating the pulse based on the pulse simulation signal, and generating different pulse states based on different pulse simulation signals. For example, the pulse simulation signal is a pulse signal detected from an individual, which is transmitted to the pulse simulator in form of the pulse simulation signal. Thus, the pulse simulator is capable of simulating a pulse on the simulated skin portion 100 for each individual. Optionally, the pulse simulator is configured to simulate a pulse for an individual based on a pulse of the individual measured in real time but in a remote location, thereby realizing haptic pulse simulation.

In one example, when the blood vessel of the individual dilates, the pulse simulator simulates the dilation of the blood vessel by an action of protruding the simulated skin portion 100 in the one or more regions of the simulated skin portion 100. When the blood vessel of the individual constricts, the pulse simulator simulates the constriction of the blood vessel by an action of having the simulated skin portion 100 fall back in in the one or more regions of the simulated skin portion 100. By controlling the frequency of the action of protruding the simulated skin portion 100 and the action of having the simulated skin portion 100 fall back in in the one or more regions of the simulated skin portion 100, a pulse wave can be simulated in the simulated skin portion 100. Optionally, the one or more regions of the simulated skin portion 100 are one or more regions of the simulated skin portion 100 having a shape similar to one or more blood vessels in the individual, e.g., on the wrist of the individual.

As compared to the conventional pulse simulator, the present pulse simulator can simulate pulses corresponding to different physiological states of different individuals. The pulse simulation in the present pulse simulator is capable of simulating various pulse states including pulses corresponding to different blood vessel sizes and different blood viscosities. Sizes of the simulated blood vessels are not strictly defined by the synthetic rubber blood vessels having a fixed shape as in the conventional pulse simulator, and the blood viscosities are not limited by the liquid filled in the synthetic blood vessels. Accordingly, accurate and personalized pulse simulation can be made possible in the present pulse simulator.

Figure 2:
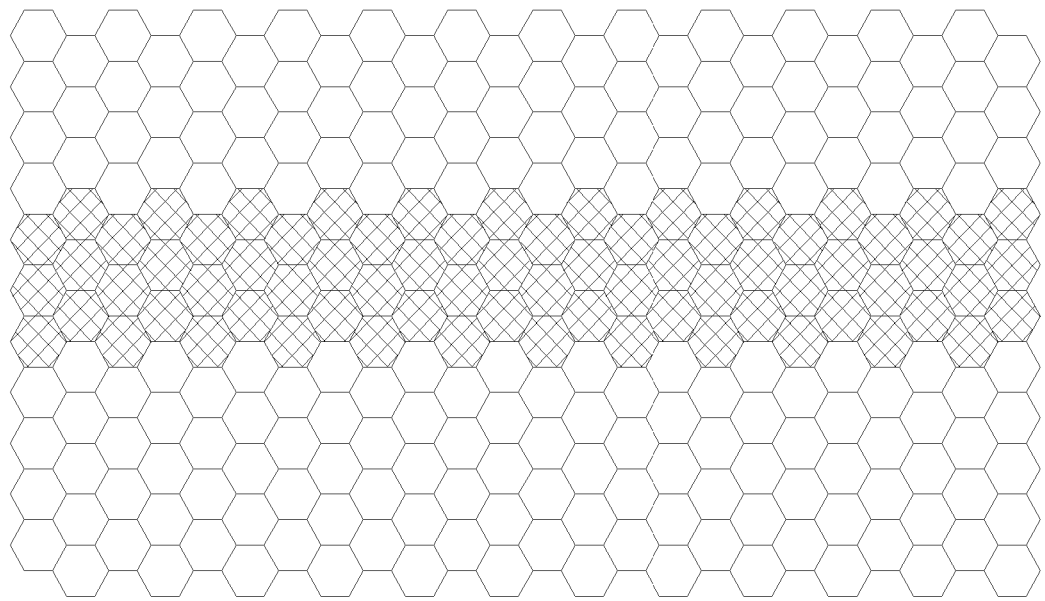
FIG. 2 is a schematic diagram illustrating a shape of a simulated blood vessel simulated by a pulse simulator in some embodiments according to the present disclosure.
Figure 3:
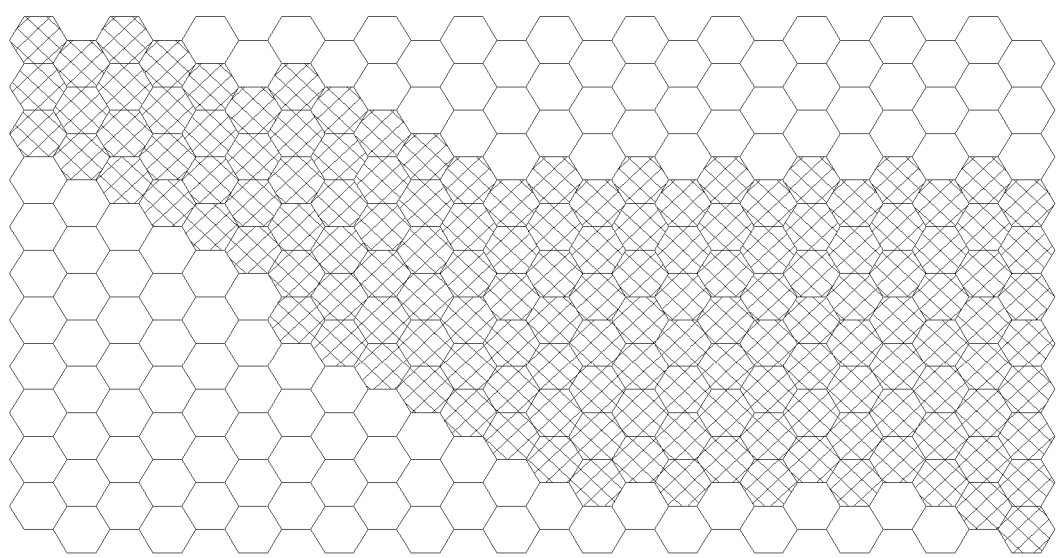
FIG. 3 is a schematic diagram illustrating a shape of a simulated blood vessel simulated by a pulse simulator in some embodiments according to the present disclosure.

Each of FIG. 2 and FIG. 3 is a schematic diagram illustrating a shape of a simulated blood vessel simulated by a pulse simulator in some embodiments according to the present disclosure. Referring to FIG. 2 and FIG. 3, the present pulse simulator is capable of simulating pulses corresponding to different shapes (as well as different sizes) of blood vessels in different individuals. The simulated blood vessels in FIG. 2 and FIG. 3 correspond to different physiological states of different blood vessels in different individuals.

Various appropriate pulse simulation signals may be used in the present pulse simulator. Examples of appropriate pulse simulation signals include a pulse wave signal (e.g., a signal indicating a frequency of a pulse wave, a signal indicating an amplitude of the pulse wave), a signal indicating a blood vessel shape, a signal indicating blood viscosity and a signal indicating blood flow speed, and so on. By including one or more (optionally all) of these signals in the pulse simulation signal, the pulse simulator can simulate a pulse that is highly realistic, facilitating haptic pulse detection and diagnosis of diseases.

Various appropriate pulse simulation assemblies may be used for simulating the pulse. Referring to FIG. 1, the pulse simulation assembly 20 in some embodiments includes a mounting plate 200; a plurality of retractable bolts 300 on the mounting plate 200; and a plurality of drivers 900 coupled to the plurality of retractable bolts 300. The plurality of retractable bolts 300 is between the simulated skin portion 100 and the mounting plate 200. Optionally, each of the plurality of retractable bolts 300 has a first end attached to the mounting plate 200 and a second end configured to be in contact with the simulated skin portion 100. Each of the plurality of drivers 900 is configured to drive one of the plurality of retractable bolts 300 to retract and extend between a first position and a second position thereby adjusting a distance between the simulated skin portion 100 and the mounting plate 200 in a region corresponding to the one of the plurality of retractable bolts 300.

Upon receiving the pulse simulation signal, the plurality of drivers 900 are configured to control some of the plurality of retractable bolts 300 to extend and retract, thereby simulating a pulse in a blood vessel. Optionally, each of the plurality of retractable bolts 300 can be individually controlled, e.g., by one of the plurality of drivers 900. By individually controlling the extension and retraction of each of the some of the plurality of retractable bolts 300, a blood vessel can be simulated to have a shape and pulsing state highly similar to a patient's blood vessel. Optionally, the patient is an individual in a remote location having her or his pulse being detected in real time, and the detected pulse signal is transmitted to the pulse simulator as the pulse simulation signal. By individually controlling the extension and retraction of each of the plurality of retractable bolts 300 in regions corresponding to the simulated blood vessel, the shape of the blood vessel of the patient can be accurately simulated. Adding to that with one or any combination of the signal indicating a blood vessel shape, the signal indicating blood viscosity, and the signal indicating blood flow speed, a highly realistic pulse state can be simulated.

In one example, when the blood vessel of the patient dilates, the plurality of drivers 900 control the some of the plurality of retractable bolts 300 to extend, pushing the simulated skin portion 100 in the region corresponding to the simulated blood vessel outwards. The distance between the simulated skin portion 100 and the mounting plate 200 in the region corresponding to the simulated blood vessel increases. In another example, when the blood vessel of the patient constricts, the plurality of drivers 900 control the some of the plurality of retractable bolts 300 to retract, the simulated skin portion 100 in the region corresponding to the simulated blood vessel falls back in. The distance between the simulated skin portion 100 and the mounting plate 200 in the region corresponding to the simulated blood vessel decreases. By controlling the frequency of extension and retraction of the some of the plurality of retractable bolts 300 in the region corresponding to the simulated blood vessel, a pulse with a pulse wave highly similar to the patient's pulse wave can be simulated.

Various appropriate elastic materials may be used for making the simulated skin portion 100. Examples of appropriate elastic materials for making the simulated skin portion 100 include poly-silicone.

Optionally, the plurality of retractable bolts 300 are an array of a plurality of retractable bolts having a plurality of rows and a plurality of columns. By having this design, the position of each of the plurality of retractable bolts 300 can be readily defined, e.g., by assigning a coordinate to each of the plurality of retractable bolts 300.

Figure 4:
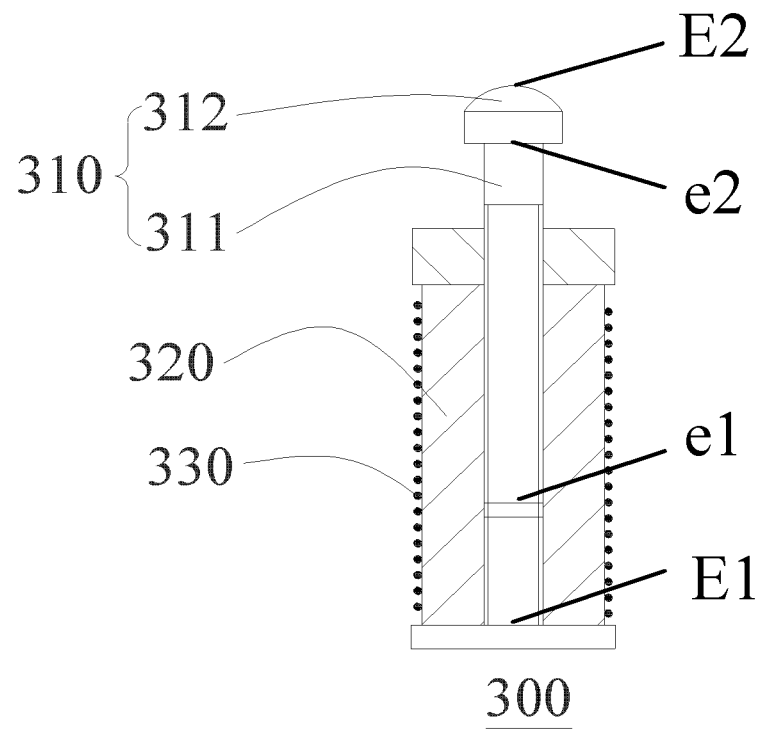
FIG. 4 is a schematic diagram illustrating the structure of a retractable bolt in some embodiments according to the present disclosure.

FIG. 4 is a schematic diagram illustrating the structure of a retractable bolt in some embodiments according to the present disclosure. Referring to FIG. 4, each of the plurality of retractable bolts 300 in some embodiments includes an actuating stem 310; a sleeve 320 surrounding the actuating stem 310; and a coil 330 around an outer surface of the sleeve 320. Optionally, the actuating stem 310 includes a magnetic main body 311. Optionally, the magnetic main body 311 has an external thread on its outer surface; and the sleeve 320 has an internal thread on its inner surface. A first end e1 of the magnetic main body 311 threadedly engaged with the sleeve 320. Optionally, each of the actuating stem 310 has a first end E1 attached to the mounting plate 200 and a second end E2 configured to be in contact with the simulated skin portion 100. The second end E2 is exposed outside the sleeve 320. One of the plurality of drivers 900 is configured to provide a current to the coil 330 to generate a magnetic field in the coil 330. Optionally, the magnetic field generated in the coil 330 has a polarity on an inner surface of the coil 330 proximal to the magnetic main body 311 opposite to the polarity of the magnetic field on an outer surface of the magnetic main body 311, and the magnetic main body 311 is magnetically attracted by the magnetic field generated in the coil 330. Optionally, the magnetic field generated in the coil 330 has a polarity on an inner surface of the coil 330 proximal to the magnetic main body 311 the same as the polarity of the magnetic field on an outer surface of the magnetic main body 311, and the magnetic main body 311 is magnetically repelled by the magnetic field generated in the coil 330.

In some embodiments, the magnetic main body 311 has a substantially cylindrical shape. When the magnetic main body 311 is attracted or repelled by the magnetic field generated in the coil 330, the magnetic main body 311 has the tendency to rotate inward or outward relative to the sleeve 320. When the magnetic main body 311 rotates outward relative to the sleeve 320, the second end E2 of the actuating stem 310 is configured to be in contact with the simulated skin portion 100. The second end E2 of the actuating stem 310 pushes the simulated skin portion 100 outward, thereby simulating a pulsing action.

In some embodiments, the second end E2 of the actuating stem 310 is attached to the simulated skin portion 100. Optionally, the extension and retraction of the actuating stem 310 drive the simulated skin portion 100 to move up and down in the region corresponding to the simulated blood vessel.

In some embodiments, the second end E2 of the actuating stem 310 is not fixedly attached to the simulated skin portion 100. For example, the second end E2 of the actuating stem 310 is separated from the simulated skin portion 100 when it retracts into the sleeve 320, and the second end E2 of the actuating stem 310 is in contact with the simulated skin portion 100 when it extends outward relative to the sleeve 320 to a certain height. In one example, the actuating stem 310 pushes the simulated skin portion 100 when it extends, and the simulated skin portion 100 falls back in by gravity when the actuating stem 310 retracts, thereby simulating the pulsing action.

In some embodiments, the actuating stem 310 further includes a contact cap 312 on a second end e2 of the magnetic main body 311 opposite to the first end e1 of the magnetic main body 311. Optionally, the contact cap 312 (and the second end E2 of the actuating stem 310) is not fixedly attached to the simulated skin portion 100. Optionally, the contact cap 312 has a convex curved surface protruding toward the simulated skin portion 100. By having a convex curved surface, any scratch on the simulated skin portion 100 caused by the movements of the actuating stem 310 can be minimized or reduced. Optionally, the contact cap 312 is made of a resin material.

Various appropriate drivers may be used for driving the plurality retractable bolts. Optionally, the plurality of drivers 900 are a plurality of electrical drivers configured to provide a current to coil 330 in each of the plurality of retractable bolts 300. Other types of drivers may be used, e.g., mechanical drivers, ultrasonic drivers, and optical drivers, and so on. Optionally, the plurality of drivers 900 are disposed on the mounting plate 200.

Optionally, the plurality of drivers 900 are an array of a plurality of drivers having a plurality of rows and a plurality of columns. Optionally, each of the plurality of drivers 900 corresponds to one or more of the plurality of retractable bolts 300. Optionally, each of the plurality of drivers 900 corresponds to a different one of the plurality of retractable bolts 300, e.g., each of the plurality of retractable bolts 300 may be individually controlled with a different driving signal.

In an in-person, face-to-face, pulse detection situation, a doctor may place her or his fingers on the patient's wrist, and apply a pressure on the wrist, to detect the pulse of the patient. Similarly, in the present, pulse simulator, a plurality of pressure sensors are provided to sense an applied pressure on the simulated skin portion 100 (e.g., on top of the simulated blood vessels as shown in FIG. 2 and FIG. 3). Referring to FIG. 1, the pulse simulator in some embodiments further includes a plurality of pressure sensors 400 mounted on the simulated skin portion 100. The plurality of pressure sensors 400 are configured to detect a pressure applied on the simulated skin portion 100. Optionally, each of the plurality of pressure sensors 400 are configured to generate a pressure simulation signal based on the detected pressure.

In some embodiments, the simulated skin portion 100 is used as a support for mounting the plurality of pressure sensors 400. Optionally, the plurality of pressure sensors 400 are disposed on an outer surface of the simulated skin portion 100. Optionally, the plurality of pressure sensors 400 are embedded in the simulated skin portion 100. Optionally, the plurality of pressure sensors 400 are disposed on an inner surface of the simulated skin portion 100. The plurality of pressure sensors 400 may be distributed (e.g. evenly) throughout the simulated skin portion 100.

In some embodiments, and as discussed in greater details below, the present disclosure further provides a pulse sensor to be used in combination with the pulse simulator. In some embodiments, the plurality of pressure sensors 400 detect the pressure applied on the simulated skin portion and generate a pressure simulation signal based on the pressure applied on the simulated skin portion. The pressure simulation signal is transmitted to the pulse sensor (e.g., a pulse sensor in a different location). Upon receiving the pressure simulation signal, the pulse sensor is configured to simulate a pressure based on the received pressure simulation signal, and applies the simulated pressure, e.g., on a wrist of a patient wearing the pulse sensor. By having the plurality of pressure sensors 400, the pulse information of the patient can be detected more accurately, facilitating medical diagnosis using the pulse simulator.

Accordingly, in another aspect, the present disclosure further provides a pulse sensor. In some embodiments, the pulse sensor includes an inflatable cuff; a plurality of pulse wave pressure sensors on an inner surface of the inflatable cuff and configured to detect a pulse wave and generate a pulse wave signal; and a first controller configured generate a pulse simulation signal based on the pulse wave signal from the plurality of pulse wave pressure sensors.

Figure 5:
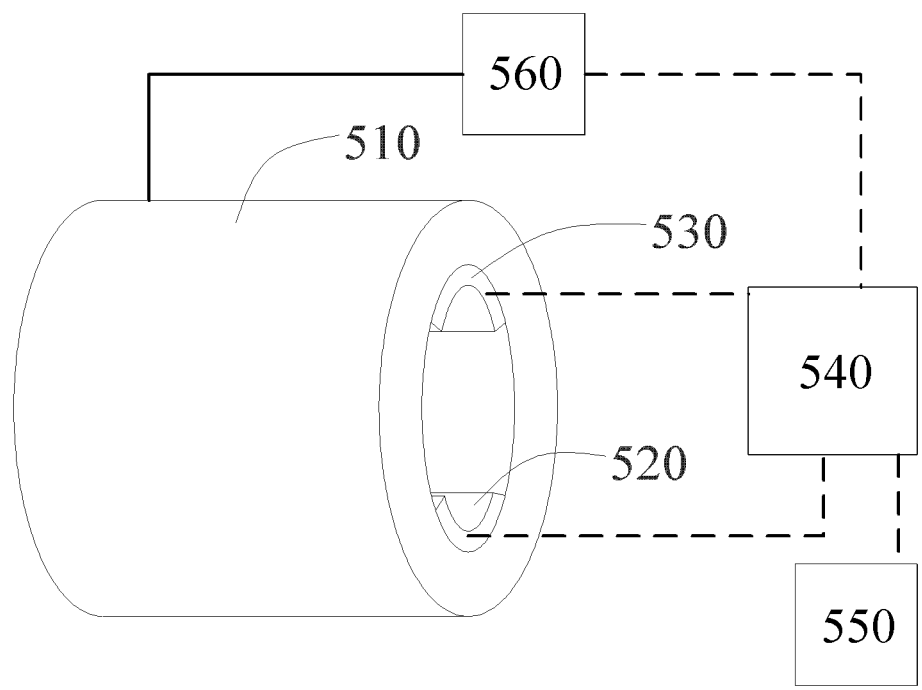
FIG. 5 is a schematic diagram illustrating the structure of a pulse sensor in some embodiments according to the present disclosure.
Figure 6:
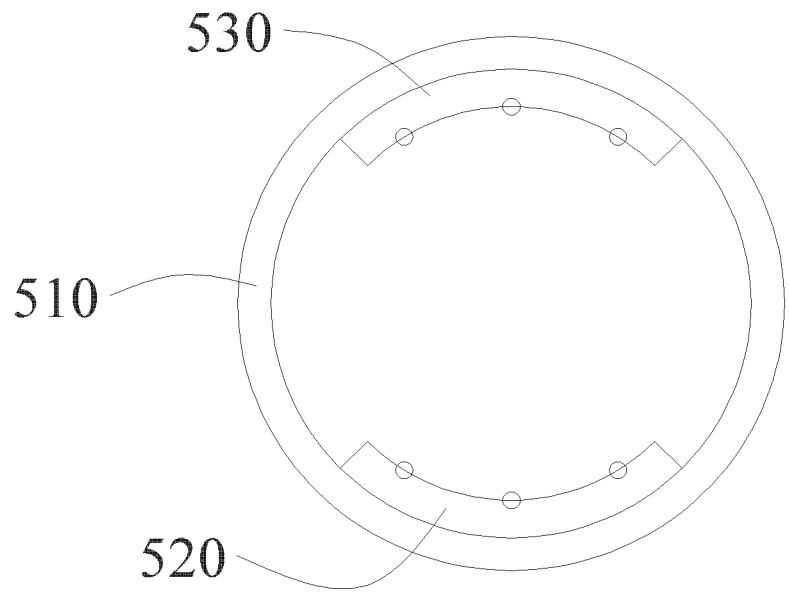
FIG. 6 is an end view of the pulse sensor in FIG. 5.

FIG. 5 is a schematic diagram illustrating the structure of a pulse sensor in some embodiments according to the present disclosure. FIG. 6 is an end view of the pulse sensor in FIG. 5. Referring to FIG. 5 and FIG. 6, the pulse sensor in some embodiments includes an inflatable cuff 510, and a plurality of pulse wave pressure sensors 520 on an inner surface of the inflatable cuff 510 and configured to detect a pulse wave and generate a pulse wave signal based on the pulse wave. In some embodiments, the pulse sensor further includes a first controller 540 configured generate a pulse simulation signal based on the pulse wave signal from the plurality of pulse wave pressure sensors 520. The first controller 540 is coupled (e.g., communicatively coupled to, wirelessly or by wire) to the plurality of pulse wave pressure sensors 520, and collects the pulse wave signal from the plurality of pulse wave pressure sensors 520.

In some embodiments, the pulse sensor is used for detecting a pulse wave in a patient. In practice, the pulse sensor may be worn by the patient, the inflatable cuff 510 may be worn around the wrist of the patient, with the plurality of pulse wave pressure sensors 520 facing the inner wrist of the patient. The inflatable cuff 510 is inflated, the pulse wave pressure sensors 520 detect the pulse wave and generate a pulse wave signal.

In some embodiments, the pulse sensor and the pulse simulator may be used in combination. The pulse sensor generates a pulse simulation signal based on the pulse wave signal from the plurality of pulse wave pressure sensors 520. The pulse simulation signal is transmitted to the pulse simulator. The pulse simulator simulates a pulse on the simulated skin portion 100 based on the pulse simulation signal received from the pulse sensor.

In some embodiments, the pulse simulation signal includes a pulse wave signal. Optionally, the pulse simulation signal further includes one or any combination of a plurality of signals respectively indicating a blood vessel shape, blood viscosity, and blood flow speed.

Various appropriate pumps may be used for pumping the inflatable cuff 510. Examples of appropriate pumps for pumping the inflatable cuff 510 include an electric pump and a mechanical pump (e.g., a balloon pump).

In some embodiments, the pulse simulation signal includes a signal indicating a blood vessel shape. Optionally, the pulse wave signal includes a signal indicating a frequency of a pulse wave, a signal indicating an amplitude of the pulse wave, and a signal indicating an address of any one of the plurality of pulse wave pressure sensors detecting the pulse wave.

In some embodiments, the location of each of the plurality of pulse wave pressure sensors 520 is fixed, e.g., relative to each other. Optionally, the first controller 540 is configured to determine the blood vessel shape based on the address of the one of the plurality of pulse wave pressure sensors 520.

Optionally, the pulse sensor further includes an imaging device, e.g., on the inner surface of the inflatable cuff 510, for obtaining an image of the patient's wrist (e.g., the inner wrist). The image of the wrist may be transmitted to a doctor at a different location for haptic diagnosis of the patient. The shape of the blood vessel can be further ascertained by viewing the image which shows the shape of the blood vessel.

In some embodiments, the inflatable cuff 510 is inflated with a pressure such that the plurality of pulse wave pressure sensors 520 are pressed against the inner wrist of the patient to facilitate detection of the pulse wave, and a simulated pressure from the pulse sensor (e.g., simulating a pressure applied by a doctor to the pulse simulator) can be passed onto the wrist of the patient wearing the inflatable cuff 510.

In some embodiments, the pulse sensor further includes a plurality of reference pressure sensors 530 on the inner surface of the inflatable cuff 510 and configured to detect a pressure applied by the inflatable cuff 510, e.g., when the inflatable cuff 510 is inflated by a pump, to a patient. Optionally, the plurality of reference pressure sensors 530 are disposed at a location opposite to that of the plurality of pulse wave pressure sensors 520 on the inner surface of the inflatable cuff 510. The plurality of reference pressure sensors 530 are configured to generate a stop signal based on a determination that the pressure applied by the inflatable cuff 510 detected by the plurality of reference pressure sensors 530 is greater than a threshold value. Optionally, a pressure applied by the inflatable cuff 510 has a threshold value such that the plurality of pulse wave pressure sensors 520 are pressed against the inner wrist of the patient to facilitate detection of the pulse wave, and a simulated pressure from the pulse sensor (e.g., simulating a pressure applied by a doctor to the pulse simulator) can be passed onto the wrist of the patient wearing the inflatable cuff 510.

In some embodiments, the pulse sensor further includes an alarm 550. Optionally, the plurality of reference pressure sensors 530 are configured to transmit the stop signal to the first controller 540. Upon receiving the stop signal from the plurality of reference pressure sensors 530, the first controller 540 is configured to transmit an alarm control signal to the alarm 550. Upon receiving the alarm control signal from the first controller 540, the alarm 550 is configured to generate an alarm signal. Upon receiving the alarm signal, an operator of the pulse sensor can discontinue inflating the inflatable cuff 510. Optionally, the alarm signal is an audio signal (e.g., a signal generated by an electric bell). Optionally, the alarm signal is a visual signal a signal generated by an indication light emitting a green light).

In some embodiments, the pulse sensor further includes a pump 560 for inflating the inflatable cuff 510. A control terminal of the pump 560 is coupled to an output terminal of the first controller 540. An output terminal of each of the plurality of reference pressure sensors 530 is coupled to an input terminal of the first controller 540. The first controller 540 is configured to control the pump 560 to discontinue inflating the inflatable cuff 510 upon receiving the stop signal from the plurality of reference pressure sensors 530.

In some embodiments, the pulse simulation signal includes at least one of a signal indicating blood viscosity and a signal indicating blood flow speed. Optionally, the pulse sensor further includes an optical detection sensor on the inner surface of the inflatable cuff 510 and configured to detect at least one of the signal indicating blood viscosity and the signal indicating blood flow speed. Optionally, the optical detection sensor is disposed on a same side as the plurality of pulse wave pressure sensors 520 on the inner surface of the inflatable cuff 510, e.g., on a side opposite to that of the plurality of reference pressure sensors 530. Optionally, the optical detection sensor is configured to emit a light, and is configured to determine blood viscosity and blood flow speed based on a light reflected back to the optical detection sensor.

In another aspect, the present disclosure provides a haptic medical device. For example, the haptic medical device may be a haptic diagnosis device. In some embodiments, the haptic medical device includes a pulse simulator described herein and a second controller coupled to the plurality of drivers 900. The second controller is configured to receive a pulse simulation signal and transmit the pulse simulation signal to the plurality of drivers 900.

The present pulse simulator can simulate pulses corresponding to different physiological states of different individuals. Sizes of the simulated blood vessels are not strictly defined by the synthetic rubber blood vessels having a fixed shape as in the conventional pulse simulator, and the blood viscosities are not limited by the liquid filled in the synthetic blood vessels. Accordingly, accurate and personalized pulse simulation can be made possible in the present pulse simulator.

Figure 7:
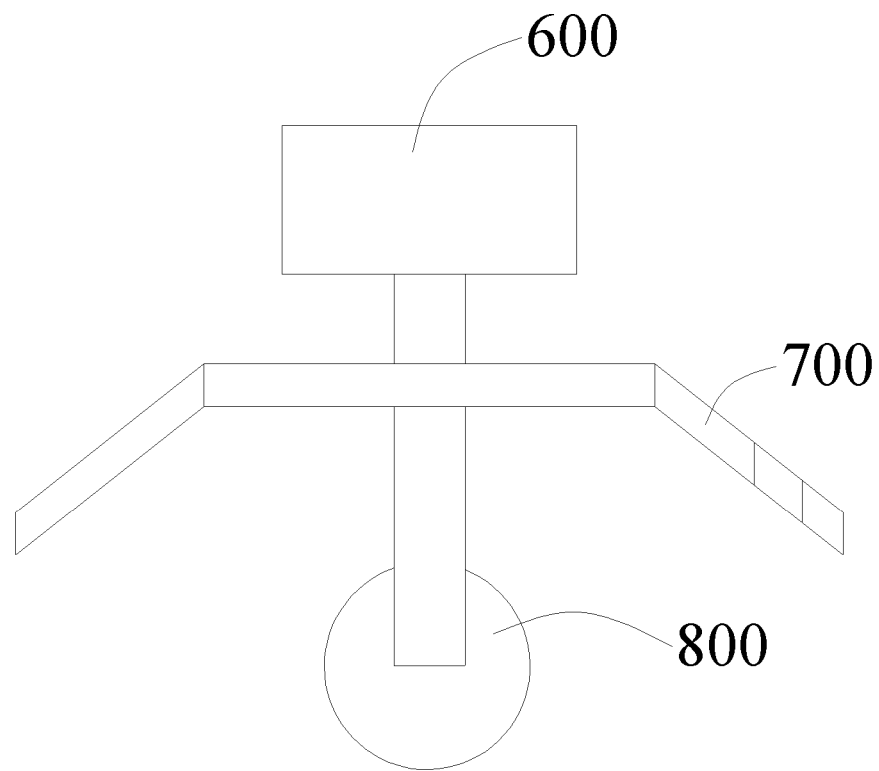
FIG. 7 is a schematic diagram illustrating the structure of a haptic medical device in some embodiments according to the present disclosure.

FIG. 7 is a schematic diagram illustrating the structure of a haptic medical device in some embodiments according to the present disclosure. Referring to FIG. 7, the haptic medical device in some embodiments further includes a display device 600 for visual data communication. For example, the display device 600 may be used for displaying the patient's body parts, the medical information of the patient, and for video conferencing with the patient. By having these visual data, the haptic diagnosis can be rendered more accurately.

In some embodiments, the haptic medical device further includes a pulse sensor. The pulse sensor detects a pulse wave of the patient and various biometric information of the patient, and generate a biometric signal. Optionally, the second controller is communicatively coupled to the pulse sensor and is configured to receive the biometric signal from the pulse sensor.

In some embodiments, the haptic medical device further includes the pulse sensor described herein. Optionally, the second controller is communicatively coupled to the first controller 540 and is configured to receive the pulse simulation signal from the first controller 540.

Referring to FIG. 7, the haptic medical device huffier includes a stand which includes a simulated arm 700. Optionally, the pulse simulator is disposed on the simulated arm 700. Optionally, the display device 600 is attached to the stand. Optionally, the haptic medical device fluffier includes a wheel 800.

In some embodiments, the pulse simulator is configured to detect a pressure applied on the simulated skin portion 100 and generate a pressure simulation signal based on the pressure applied on the simulated skin portion 100. The second controller is configured to receive the pressure simulation signal and transmit the pressure simulation signal to the first controller 540. The first controller 540 is configured to generate a threshold value for a threshold pressure based on the pressure simulation signal received from the second controller. Optionally, when the pressure in the inflatable cuff 510 reaches the threshold value, the pulse sensor is configured to discontinue inflating the inflatable cuff 510. Optionally, the pressure simulation signal is generated by the plurality of pressure sensors 400.

In another aspect, the present disclosure provides a method for haptic pulse detection. In some embodiments, the method includes connecting a pulse simulator and a pulse sensor at different locations to a computer network; detecting a pulse wave and generate a pulse wave signal using the pulse sensor; generating a pulse simulation signal based on the pulse wave signal; transmitting the pulse simulation signal to the pulse simulator; and simulate a pulse based on the pulse simulation signal on a simulated skin portion using the pulse simulator.

Optionally, the method further includes detecting a pressure applied on the simulated skin portion, and generating a pressure simulation signal based on the pressure applied on the simulated skin portion.

Optionally, the method further includes detect a pressure applied by an inflatable cuff of the pulse simulator, and generating a stop signal based on a determination that the pressure applied by the inflatable cuff is greater than a threshold value. Optionally, the method further includes discontinuing inflating the inflatable cuff upon receiving the stop signal from the plurality of reference pressure sensors.

Optionally, the method further includes detecting at least one of the signal indicating blood viscosity and the signal indicating blood flow speed.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A pulse simulator, comprising:
a pulse simulation assembly configured to receive a pulse simulation signal and simulate a pulse of a living body based on the pulse simulation signal;
wherein the pulse simulation assembly comprises:
a mounting plate;
a plurality of retractable bolts on the mounting plate; and
a plurality of drivers coupled to the plurality of retractable bolts;
wherein a respective one of the plurality of retractable bolts has a first end attached to the mounting plate and a second end opposite to the first end; and
a respective one of the plurality of drivers is configured to drive one of the plurality of retractable bolts to retract and extend between a first position and a second position thereby adjusting a distance between a simulated skin portion and the mounting plate in a region corresponding to the one of the plurality of retractable bolts
wherein the respective one of the plurality of retractable bolts comprises:
an actuating stem;
a sleeve surrounding the actuating stem; and
a coil around an outer surface of the sleeve;
wherein the actuating stem comprises a magnetic main body;

the magnetic main body has an external thread on its outer surface;

the sleeve has an internal thread on its inner surface;

a first end of the magnetic main body threadedly engaged with the sleeve;

one of the plurality of drivers is configured to provide a current to the coil to generate a magnetic field in the coil; and the magnetic main body is configured to rotate relative to the sleeve upon application of the current to the coil.

2. The pulse simulator of claim 1, further comprising a simulated skin portion coupled to the pulse simulation assembly;

wherein the second end of the respective one of the plurality of retractable bolts is configured to be in contact with the simulated skin portion; and the pulse simulation assembly is configured to simulate the pulse of a living body on the simulated skin portion based on the pulse simulation signal.

3. The pulse simulator of claim 1, wherein the plurality of retractable bolts are an array of a plurality of retractable bolts comprising a plurality of rows and a plurality of columns.

4. The pulse simulator of claim 1, wherein the pulse simulation signal comprises a combination of a plurality of signals respectively indicating a pulse wave signal, a blood vessel shape, blood viscosity, and blood flow speed.

5. The pulse simulator of claim 1, wherein the actuating stem further comprises a contact cap on a second end of the magnetic main body opposite to the first end of the magnetic main body; and the contact cap has a convex curved surface protruding outward along a direction away from the mounting plate.

6. The pulse simulator of claim 1, wherein the plurality of drivers are on the mounting plate.

7. The pulse simulator of claim 2, further comprising:

a simulated skin portion coupled to the pulse simulation assembly; and a plurality of pressure sensors mounted on the simulated skin portion, and configured to detect a pressure applied on the simulated skin portion and generate a pressure simulation signal based on the pressure applied on the simulated skin portion.

8. The pulse simulator of claim 1, wherein the pulse simulation signal comprises a pulse wave signal.

9. The pulse simulator of claim 8, wherein the pulse simulation signal further comprises one or any combination of a plurality of signals respectively indicating a blood vessel shape, blood viscosity, and blood flow speed.

* * * * *